United States Patent [19]

Prager

[11] Patent Number: 5,066,798

[45] Date of Patent: Nov. 19, 1991

[54] CRYSTALLINE CEPHALOSPORIN DERIVATIVE

[75] Inventor: Bernhard C. Prager, Wörgl, Austria

[73] Assignee: Biochemie Gesellschaft m.b.H., Tyrol, Austria

[21] Appl. No.: 538,795

[22] Filed: Jun. 15, 1990

Related U.S. Application Data

[60] Continuation of Ser. No. 458,279, Dec. 28, 1989, abandoned, which is a continuation of Ser. No. 336,278, Apr. 11, 1989, abandoned, which is a division of Ser. No. 57,552, Jun. 3, 1987, Pat. No. 4,826,972.

[30] Foreign Application Priority Data

Jun. 4, 1986 [AT] Austria .................................. 1511/86

[51] Int. Cl.$^5$ ................. C07D 501/38; A61K 31/545

[52] U.S. Cl. .................................................... 540/225
[58] Field of Search ........................................ 540/225

[56] References Cited

FOREIGN PATENT DOCUMENTS 8504659 10/1985 World Int. Prop. O. .

Primary Examiner—Nicholas S. Rizzo
Attorney, Agent, or Firm—Gerald D. Sharkin; Robert S. Honor; Thomas O. McGovern

[57] ABSTRACT

The invention provides crystallilne (6R, 7R)-7-[[2 ( 2-Amino-4-thiazolyl)-(Z)-2-(1-diphenylmethoxycarbonyl-1-methylethoxy)imino]acetamido]-3-(1--pyridiniummethyl)-3-cephem-4-carboxylate and a process for its production.

2 Claims, No Drawings

CRYSTALLINE CEPHALOSPORIN DERIVATIVE

This is a continuation of application Ser. No. 07/458,279, filed Dec. 28, 1989, now abandoned which in turn is a continuation of application Ser. No. 07/336,278, filed Apr. 11, 1989, now abandoned which in turn is a division of application Ser. No. 07/057,552, filed June 3, 1987, now U.S. Pat. No. 4,826,972.

The present invention provides a new crystalline, highly pure and stable form of the syn-isomer of the cephalosporin derivative of formula

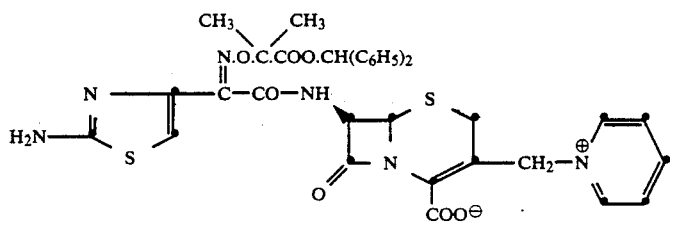

as well as a process for its production.

The cephalosporin derivative of formula I is useful as an intermediate for the production of highly active cephalosporin antibiotics which can be administered parenterally and show a very broad spectrum of activity against pathogenic microorganisms, particularly in the gram negative area.

The syn-isomer compound of formula I has usually been isolated in the form of a salt, such as the dihydrochloride or chloride hydrochloride. Hitherto, the free betaine form has only been isolated from complex solvent mixtures which has resulted in a product, in particular a solvate, with less than optimal purity and stability. It has now surprisingly been found that the syn-isomer of the compound of formula I can be isolated in free betaine form, and free of acid or solvent adducts, in excellent yield and purity ($\geq 97\%$) as a stable highly crystalline product, direct from the reaction mixture used to produce it. The product has the physical characteristics set out in the Example hereinafter.

The present invention provides more particularly a process for the production of the syn-isomer of compound of formula I in crystalline form, comprising reacting the syn-isomer of a compound of formula II and/or IIa

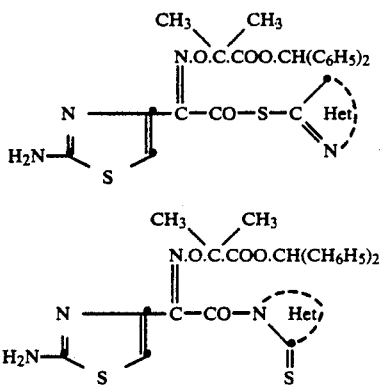

in which

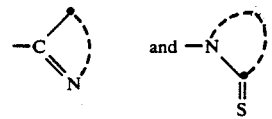

signify a 5- or 6-membered heterocyclic ring which may contain in addition to the nitrogen atom one or two further hetero atoms for example oxygen, nitrogen or sulphor, and which may be substituted, and which may be fused to a benzene ring which may itself be substituted, with a compound of formula III,

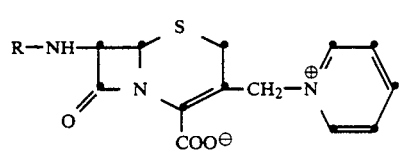

in which R is hydrogen or an amino protecting group, or a salt thereof, e.g. the hydrochloride, mixing the resulting reaction mixture with a mixture of an acetic acid ester and a lower alkanol at a temperature of from 0° to 40° C., preferably 15° to 25°, and recovering the precipitated product. In this manner, the product crystallises out in a matter of a few minutes to a few hours in practically quantitative yield and high purity ($\geq 97\%$ yield and purity). Preferred acetic acid esters include $C_{1-6}$ alkyl acetates, preferably ethyl, propyl and butyl acetate. Preferred lower alkanols include ethanol and particularly, methanol. The ratio of acetate to lower alkanol to reaction mixture depends on the chosen acetate and alkanol but is usually about 2-3:1:1 by volume, particularly in the case of ethyl or butylacetate and methanol.

The nature of the "Het" ring in the compounds II and IIa is not critical, the preferred compounds being determined by such factors as availability of starting materials and ease of production. The preferred rings are 2-pyridyl and, in particular 2-benzylthiazolyl or less preferably pyrimidinyl, triazolyl or thiazolyl, and the corresponding thiones as in compounds IIa.

The compounds of formula II, IIa and III are known and may be produced in conventional manner.

In the following Example, which illustrates the invention of all temperatures are in °C.

EXAMPLE (6R, 7R)-7-[[2-(2-Amino-4-thiazolyl)-(Z)-2-(1-diphenylmethoxycarbonyl-1-methylethoxy)imino]acetamido]-3-(1pyridiniummethyl)-3-cephem-4-carboxylate 212 g of 2-(2-Amino-4-thiazolyl)-(Z)-2-(1-diphenylmethoxycarbonyl-1-methylethoxy)iminoacetic acid are suspended together with 138 g of triphenylphosphine in 800 ml of methylene dichloride, the mixture is cooled to 0° and 175 g of mercaptobenzthiazole disulphide are added. After 2 hours stirring at 0°, the formation of the thioester II or the corresponding compound IIa is complete (as determined by DC) and 260 g of 7-amino-3-pyridiniummethylcephalosporanic acid hydrochloride and 61 g of triethylamine are added at 0°. The mixture is stirred for 15 hours at 0° until the reaction is complete (as determined by HPLC) and the reaction mixture (yellow-brown) (ca. 1400 ml) is introduced into a mixture of 1400 ml of methanol and 3.5 liters of butylacetate at about 20°. The resulting clear solution is stirred at room temperature for 2 hours and then at 0° for a further 2 hours. The resulting highly crystalline precipitate is filtered off, washed with cold methanol and dried in vacuo. The highly pure ($\geq 97\%$) by weight, free-flowing heading compound results.

What is claimed is:

1. Crystalline (6R, 7R)-7 -2-(2-Amino-4-thiazolyl)-(Z)-2-(1-diphenylmethoxycarbonyl-1-methylethoxy)imino acetamido -3-(1-pyridiniummethyl)-3-cephem-4-carboxylate.

2. The product of claim 1 in a purity of at least 97%.